United States Patent [19]

Jarman et al.

[11] Patent Number: 5,372,042
[45] Date of Patent: Dec. 13, 1994

[54] ULTRASONIC INSPECTION OF SEAL INTEGRITY OF BOND LINES IN SEALED CONTAINERS

[75] Inventors: David Jarman, Oswego, N.Y.; Bahram Farahbakhsh, Kingston; Ralph Herzig, Ottawa, both of Canada

[73] Assignee: Alcan International Limited, Montreal, Canada

[21] Appl. No.: 842,364

[22] PCT Filed: Sep. 21, 1990

[86] PCT No.: PCT/CA90/00314

§ 371 Date: May 12, 1992

§ 102(e) Date: May 12, 1992

[87] PCT Pub. No.: WO91/05250

PCT Pub. Date: Apr. 18, 1991

[30] Foreign Application Priority Data

Sep. 29, 1989 [CA] Canada ................. 615294

[51] Int. Cl.$^5$ .............. G01N 29/08; G01N 29/20; G01N 29/26
[52] U.S. Cl. .......................... 73/588; 73/599
[58] Field of Search .............. 73/588, 599, 600, 582, 73/609, 610, 614, 645, 646

[56] References Cited

U.S. PATENT DOCUMENTS

| | | | |
|---|---|---|---|
| 2,971,372 | 2/1961 | Lewis et al. | 73/610 |
| 3,384,767 | 5/1968 | Arnold et al. | 73/600 |
| 4,457,174 | 7/1984 | Bar-Cohen et al. | 73/582 |
| 4,750,368 | 6/1988 | Shearer et al. | 73/600 |
| 4,821,573 | 4/1989 | Nagata et al. | 73/597 |

FOREIGN PATENT DOCUMENTS

| | | |
|---|---|---|
| 85023 | 1/1983 | Australia . |
| 2757355 | 7/1979 | Germany . |
| 0186753 | 9/1985 | Japan . |
| 2194041 | 2/1988 | United Kingdom . |

OTHER PUBLICATIONS

"On-line Detection of Food Container Faults" by J. D. Selman, R&D Review (Feb. 1987).
"Possibilities of Testing Lap-Welded Joints In Thermoplastic Sealing" by S. Langrock, Zis Mitteilungen (vol. 25, iss. 8, 1983) pp. 796–803.

*Primary Examiner*—Hezron E. Williams
*Assistant Examiner*—Rose M. Finley
*Attorney, Agent, or Firm*—Cooper & Dunham

[57] ABSTRACT

A method for determining bond integrity of a sealed package has a lid bonded to a container rim by detecting flaws in the bond between the lid and the container. The method comprises: i) positioning the container rim between an ultrasonic transmitter system and an ultrasonic receiver system; ii) ultrasonically coupling the transmitter system and the receiver system to the container rim; iii) transmitting ultrasound waves from the transmitter system through the container rim to the receiver system; iv) generating a signal representative of the ultrasound waves received by the receiver system; and v) analyzing the signal for predetermined signal characteristics representative of a flaw in the bond to identify a flawed package seal.

4 Claims, 8 Drawing Sheets

FIG.9A. DEFECT FREE

FIG.9B. SILICON GREASE

FIG.9C. DEFECT FREE

FIG.9D. TEFLON INSERT

FIG.9E. DEFECT FREE

FIG.9F. MEAT FIBRES

ULTRASONIC INSPECTION OF SEAL INTEGRITY OF BOND LINES IN SEALED CONTAINERS

FIELD OF THE INVENTION

This invention relates to the non-destructive testing of bond integrity of a sealed package having a lid bonded to the container rim.

BACKGROUND OF THE INVENTION

A variety of containers are used to package substances which are sensitive to air to ensure extended shelf-life of the contained product. The seal for the lid of the container must be complete to ensure viability of the contents. This is particularly important in the field of packaging food and other comestibles and medical products and the like. Containers, which are particularly sensitive to defects in container seal, are those containers where a lid is welded or glued to the container rim. Such types of containers are used for packaging a variety of food products, such as meal portions, pet foods, dairy products and the like, as well as liquids usually in the form of medications and cosmetics.

There are presently available a variety of techniques which may be used to test the integrity of the container seal to ensure extended shelf life of the contained product. Such testing procedures include application of a pressure differential to the container exterior and thereby ascertain whether or not there are leaks at the bond of the lid to the container. The pressure differential may be applied by either drawing a vacuum on or applying pressure to the container. This testing procedure only works with rigid or semi-rigid containers. Soft containers are either crushed or blowout. Container defects may also be determined by way of costly visual inspection which cannot check internal aspects of the seal. X-ray imaging may also be used, but is of questionable worth and does not work with aluminum laminates.

It has been suggested in the publication R and D, Selman, J. D. "On-Line Detection of Food Container Faults" February, 1987, that optical equipment could be used to provide measurement of the seam dimensions by use of fibre optics systems or lasers to detect seal faults. Thermo-imaging is another technique that may have application in determining flaws in the seal, but it has been found to be too insensitive. The thermal properties of trapped defects, such as meat fibres and bond line materials, are similar. It is also suggested in this reference that ultrasonics could be used to measure the internal seam bond structure of the lidded container. There is no discussion, however, in the reference of the manner in which ultrasonic testing equipment could be used in detecting flaws in the seal of the container.

Published U.K. patent application 2,029,960 (Mar. 26, 1980) discloses an ultrasonic testing device for testing claddings, solder joints, adhesive points other types of surface connections. The device is particularly suited for testing solder joints. A transmitting transducer is coupled to the bonded surface via coupling medium. On the other side of the bond, a receiving transducer is coupled via a coupling medium. Adaptors may be used to conform to the geometric shape of the bonded item. The received ultrasonic sound is converted into a signal which is displayed by the apparatus as a sound intensity. A drop in sound intensity indicates that the bond is not complete and hence faulty.

Langrock et al disclose in a report from the Central institute for Welding Technology of the DDR in Halle entitled "Possibilities of Testing Lap-Welded Joints in Thermoplastic Sealing Strips" that a reflective form of electrosonic tester unit would be useful in detecting faults in lap-joints of plastic material. Pulse wave forms generated by the testing equipment are analyzed to detect defects in the welded lap-joint of similar plastic materials. The pulse echo mode of operation is effective with this type of lap-joint in view of the thickness of the films which can be in excess of 1 to 2 mm. By analyzing the reflection of the ultrasonic energy, evaluation can be made in the uniformity of the lap-joint in the sealed plastic surfaces. However, the echo system would not be sufficiently sensitive to detect very fine defects in the joint, such as experienced in containers where meat fibers and other food fibers can be caught between the bond of the lid to the container which constitutes forming a defective seal. Compared to these thicknesses, the containers in question have a welded plastic thickness of only 15 $\mu$ with a total seam thickness of only 185 $\mu$.

SUMMARY OF THE INVENTION

According to an aspect of the invention, a method is provided for determining bond integrity of a sealed package having a lid bonded to a container rim by detecting flaws in the bond between the lid and the container. The method comprises:

i) positioning the container rim between an ultrasonic transmitter system and an ultrasonic receiver system;

ii) ultrasonically coupling the transmitter system and the receiver system to the container rim;

iii) transmitting ultrasound waves from the transmitter system through the container rim to the receiver system;

iv) generating a voltage signal representative of the ultrasound waves received by the receiver system; and v) analyzing the voltage signal for predetermined signal characteristics representative of a flaw in the bond to identify a flawed package seal.

According to another aspect of the invention, an apparatus for determining bond integrity of a sealed package has a lid bonded to a container rim. The apparatus comprises:

i) spaced-apart opposing ultrasonic transmitter system and an ultrasonic receiver system;

ii) means for positioning a container rim between the ultrasonic transmitter system and the ultrasonic receiver system; and iii) means for ultrasonically coupling the transmitter system and the receiver system to a container rim.

BRIEF DESCRIPTION OF THE DRAWINGS

Preferred embodiments of the invention are shown in the drawings wherein:

FIGS. 9(A,B), 9(C,D) and 9 (E,F) are representative signals derived from testing containers with and without seal defects.

DETAILED DESCRIPTION OF THE PREFERRED EMBODIMENTS

There are a variety of packages in which the contents are very sensitive to its environment. Not only is it important to provide a package in which the seal is assured, but also to guarantee extended shelf life, there needs to be a testing technique to determine the integrity of the seal. The testing technique is preferably performed in a non-invasive manner and also in a way which does not have the potential of destroying or weakening the seal in the process of analyzing seal integrity. According to this invention, a non-invasive ultrasonically based technique is provided. The purpose of the technique is to determine in each sealed container the integrity of the seal. If the seal passes, the container is directed for packaging whereas if the seal is flawed or defective, the container is directed for discard.

Figures 1, 1A:
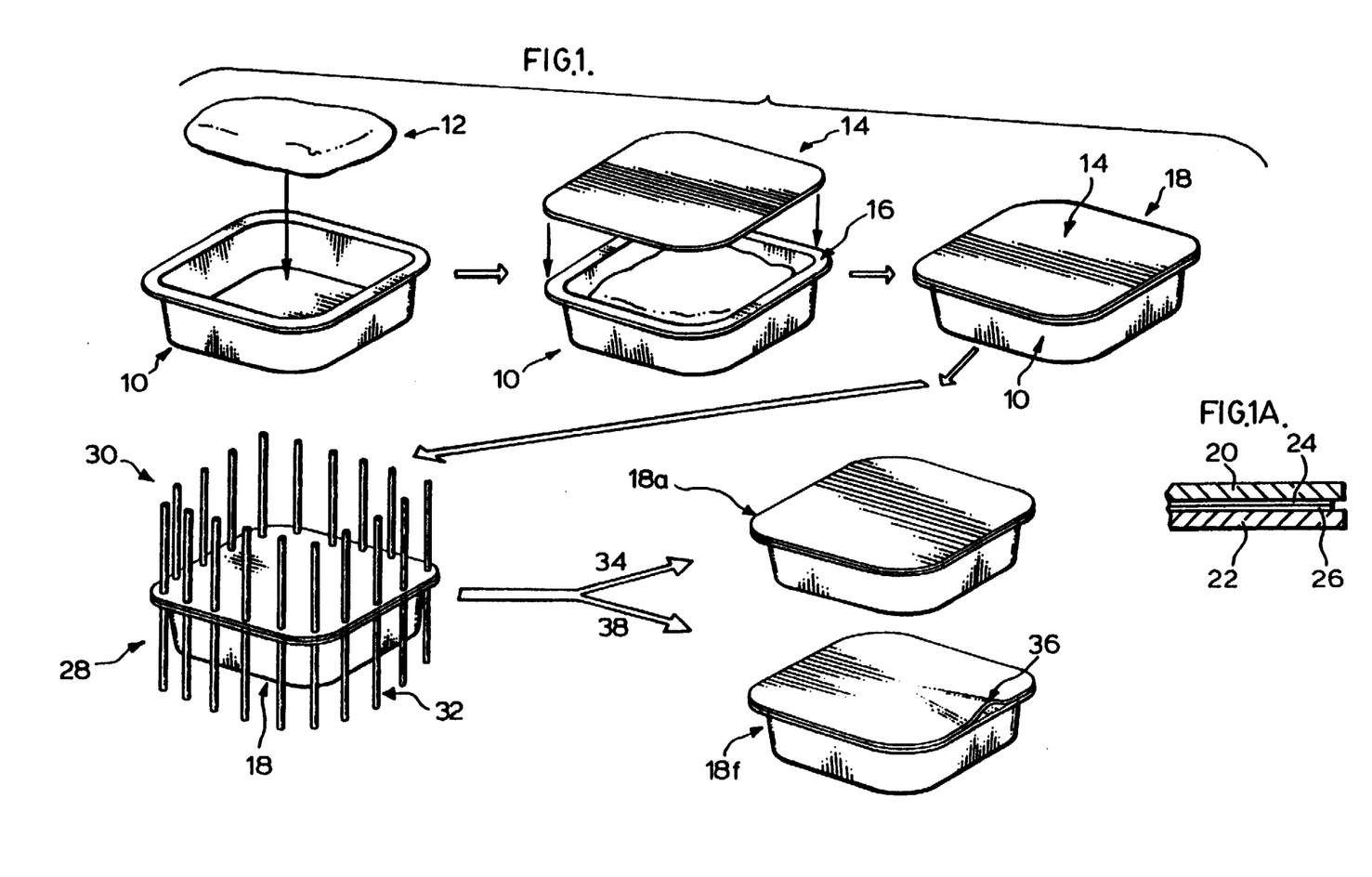
FIG. 1 is a schematic flow chart of a container being loaded with product, tested and then either passed or rejected.
FIG. 1A is an enlarged view of a section of the container rim.

As shown in FIG. 1, a container 10 has loaded therein a product 12 which, in one way or another, is sensitive to the atmosphere or environment in which it is normally placed. The next step is to seal the container 10 with a lid 14. In this embodiment, the container 10 has a circumferential rim 16 with the lid 14 applied to the rim 16 and bonded thereto. The lid 14 is of a size to at least cover the circumferential dimensions of the container rim 16. The sealed container 18 may have the lid 14 sealed to the container 10 by adhesives, welding of like materials or other known techniques in bonding of materials such as catalyzed polymerization of the similar mating materials. As shown in FIG. 1A, according to this particular embodiment, the sealed container 18 has a foil lid 20 and a foil container 22. Laminated to the opposing foils 20 and 22 are thin layers of polypropylene 24 and 26. The opposing layers of polypropylene 24 and 26, or other suitable polyolefins such as polyethylene, are heat welded together under pressure to bond the lid 14 to the container rim 16. The integrity of the bond between plastic layers 24 and 26 has to be determined in accordance with the apparatus and method of this invention. The container 18 is conveyed schematically to a testing system 28.

According to this embodiment, the perimeter of the container rim with the lid bonded thereto is placed between a system of ultrasonic transducers in the form of an array of a plurality of ultrasonic transmitter units generally designated 30 and ultrasonic receiver units generally designated 32. The ultrasonic transmitters and receivers are ultrasonically coupled to the container rim in a manner, for example, as discussed with respect to the embodiments of FIGS. 2 through 4. The ultrasonic waves are transmitted through the container rim from the transmitters 30 to the receivers 32. A signal from each receiver is then generated representative of the ultrasonic waves received by the receiver. The signal is analyzed for predetermined signal characteristics representative of a flaw in the bond to identify a flawed seal. Hence when the container leaves the sensing system, if the container is not flawed such as sealed container 18a, it is moved in the direction of arrow 34. If the container 18f is flawed as indicated diagrammatically in FIG. 1 by exaggerated bump by food residue in the seal at 36, then the container is conveyed in the direction of arrow 38. It is noted that, with the flaw in the seal of container 18f, the flaw has been exaggerated for purposes of illustration. Normally, flaws are not visible except when adherent food has been squeezed out through the seal. The good container 18a is then conveyed to a suitable packaging transport station. The flawed container 18f is conveyed for disposal.

Figure 2:
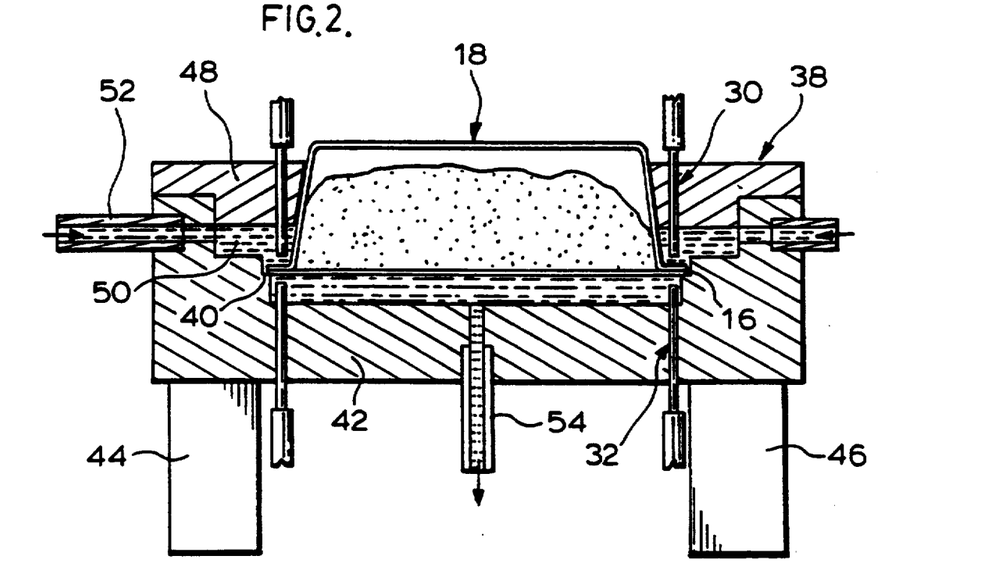
FIG. 2 is a section through an apparatus in which the method of this invention is employed to ultrasonically test the integrity of the container seal.

One suggested arrangement for detecting flaws in the container rim is shown in FIG. 2. The sealed container 18 is inverted and placed within an apparatus 38 where a liquid, preferably water, is used to ultrasonically couple the transmitter array 30 to the container rim 18 and also ultrasonically couple the receiver array 32 to the container rim 18. The container rim 16 rests on a ledge 40 which is in the shape of a container rim to thereby support the seal container 18 in the inverted position. The array of ultrasonic receivers 32 are secured in the block 42 of the apparatus which are supported by feet 44 and 46. A closure 48 for the apparatus is provided in which the transmitter array 30 is mounted. The probe portions of the transmitters and receivers extend into the space 50 which is filled with water or other suitable liquid. The water is introduced through ports 52 around the perimeter of the apparatus. Suitable valves, not shown, are provided in the conduits for the ports 52 to control flow of water into the space 50. A drain or outlet 54 is provided to drain the water from the space 50. A suitable valve may be located in the drain 54 to control flow of fluid through the drain. It is appreciated that all valves associated with the inlets and drains may be electronically controlled so that the sequence in filling the space with water and draining and maintaining water in the space during testing is all controlled automatically. With the apparatus 38 sealed and water ultrasonically coupling the transmitters and receivers to the container rim, ultrasonic waves are transmitted through the container rim and a signal generated based on the waves received by the receiver 32. The signal generated will be discussed with respect to FIGS. 8 et seq. It has been found that the use of water in the apparatus 38 provides an excellent ultrasonic coupling of the transmitter and receiver to the container rim.

Figure 3:
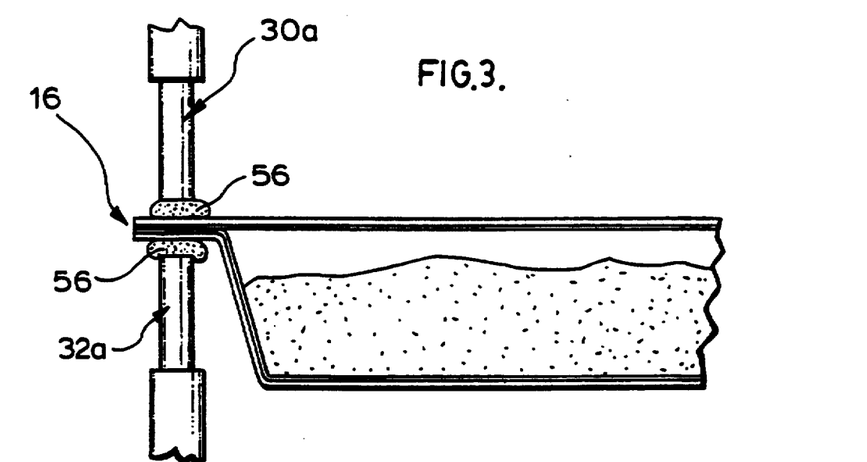
FIG. 3 shows an alternative embodiment for ultrasonically coupling the sensors to the container rim for purposes of detection.

It is appreciated, however, that other systems are available for ultrasonically coupling the probes of the transmitters and receivers to the container rim. As shown in FIG. 3, the individual transmitter 30a is ultrasonically coupled to the container rim 16 by a viscous fluid 56. The viscous fluid may be gel, oil, a jelly or the like. Similarly, the individual receiver unit 32a is ultrasonically coupled to the container rim 16 by the same viscous fluid 56. In this manner with the ultrasonic coupling of the transmitter and receiver to the container rim, a direct transmission of the ultrasonic waves are assured. Hence the system of FIG. 3 avoids the need to immerse the container rim and transmitters and receivers in water, such as exemplified in FIG. 2.

Figure 4:
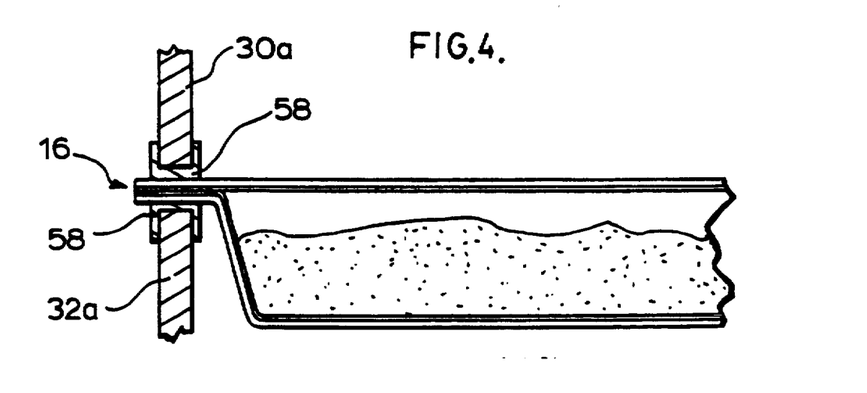
FIG. 4 shows yet another alternative embodiment for ultrasonically connecting the sensors to the container rim.

FIG. 4 shows another embodiment for ultrasonically coupling the individual transmitter 30a and individual receiver 32a to the container rim 16. Suitable elastomeric cups 58 are provided on the ends of the transmitter and receiver to ultrasonically couple the transmitter and receiver to the container rims 16. The systems of FIGS. 3 and 4 therefore provide ways of ultrasonically coupling the transmitters and receivers to the container rim to determine the integrity of the container seal without having to immerse the container in water or other ultrasonic coupling medium.

Figure 5:
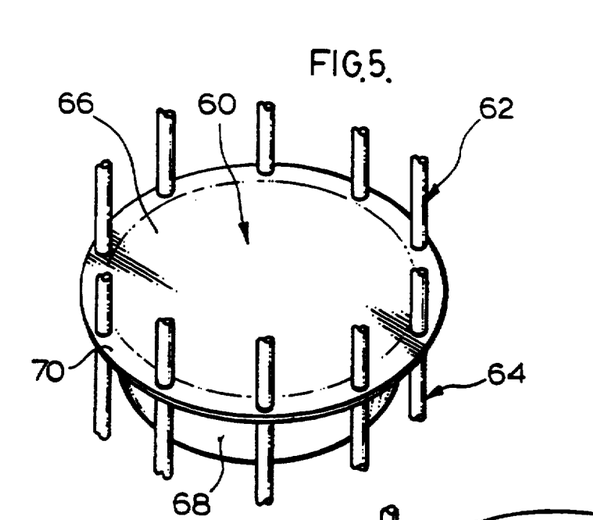
FIG. 5 is a perspective showing a container and an array of a plurality of ultrasonic transmitters and ultrasonic receivers for testing flaws in the container rim.

FIG. 5 shows a sealed circular rim container 60 which can be tested with a transmitter and receiver array 62 and 64. In this manner, the rim is tested at the locations of the transmitters and corresponding receivers to determine the presence of any flaws in the bond of the lid 66 and the container 68. The array of transmitters and receivers 62 and 64 are positioned about the container rim 70 to detect flaws in the vicinities of each of the detectors.

Figure 6:
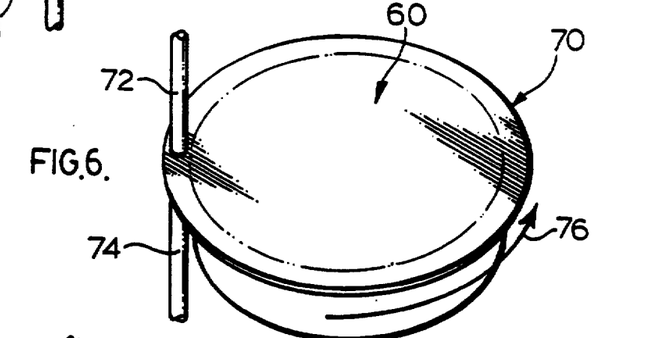
FIG. 6 shows a single ultrasonic transmitter and receiver between which the container rim is positioned and rotated to sense flaws around the entire periphery of the container rim.

An alternative set up for detecting flaws in the rim 70 of the container 60 is to position the rim between a single transmitter 72 and receiver 74 of the ultrasonic testing system as shown in FIG. 6. The transmitter and receiver are ultrasonically coupled to the rim, for example, by the techniques of FIGS. 3 or 4. The container 60 is then rotated in the direction of arrow 76 in either a continuous or stepwise manner to allow for transmission of ultrasonic waves to the container rim which are then subsequently analyzed in accordance with the procedure to be later described.

It is appreciated that a variety of other transmitter and receiver arrays may be used to provide, for example, better coverage, improved sensitivity, cost economies and the like. Such conditions may be dependent upon the characteristics of the seal to be detected. Various considerations include, for example, as an alternative to FIG. 6, the container may remain stationary and the transmitter receiver pair moved in a manner to trace the circumference of the container rim and thereby sense defects in the seal of the container rim. The transmitter and receiver arrays, such as shown in FIG. 5, can either be arranged to provide for discontinuous coverage with the spaced-apart positioning of the transmitters and receivers, or a continuous coverage where the transmitter receiver arrays are positioned very close to one another, normally proximate to each other to provide for complete coverage of the seal area. For some container configurations, a continuous or even discontinuous transmitter receiver array may be too costly. It is contemplated, in accordance with this invention, that half of the container rim is covered by the array of transmitters and receivers. Either the sensor system or the container is then rotated 180° to complete scanning of the other half of the container rim.

Figure 5A:
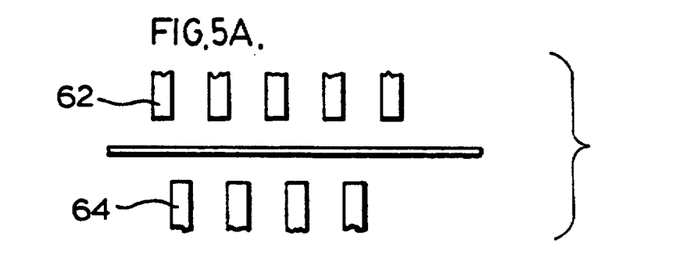
FIGS. 5A, 5B, 5C and 5D are view of alternative arrangements for the testing system of this invention.
Figure 5B:
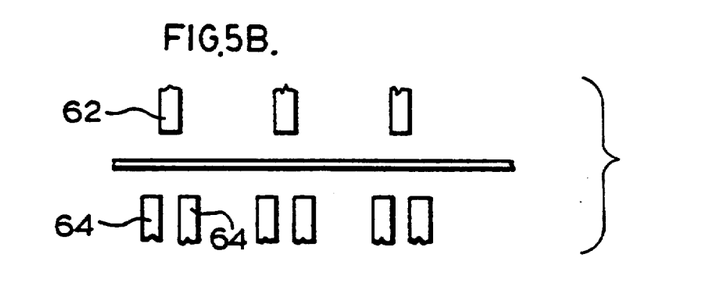

It is also appreciated that, with multiple receivers and transmitters such as the arrangement of FIG. 5, it is not necessary that the receiver be directly aligned with the transmitter. It is possible to offset the receivers relative to the transmitter to enhance the coverage of the container rim seal. As shown in FIG. 5A, the staggered arrangement for the transmitters 62 relative to the receivers 64 is such that each receiver is positioned between the transmitter 62 in terms of their general direction of transmission. Alternatively as shown in FIG. 5B, two receivers for every transmitter may be provided. Transmitter 62 is then located above two receivers 64 where the receivers are close to each other and generally aligned with the transmitter. Such arrangement provides for improved sensitivity in detecting flaws in the container seal. This arrangement also indicates another advantage of the invention in that the container rim does not have to be centered exactly between the transmitter and the receiver. Considerable leeway is permitted particularly with the immersion applications where a gap of up to 5 mm can exist. On the other hand, with prior art systems such as the echo technique, a precise location of the bond surface is always required relative to the transducer.

Figure 5C:
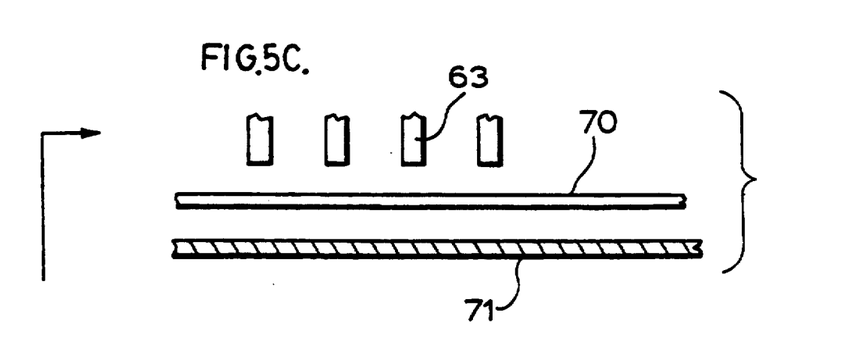

As shown in FIG. 5C, the transmitter may be either a single element or a dual element transducer. Such dual element transducer 63 transmits the ultrasonic waves through the container rim 70. Instead of locating receivers on the other side of the container rim, a reflective surface 71 is provided to reflect the ultrasonic waves back through the container rim to be received by the receiving portion of the dual element transducer 63. This is in keeping with the invention where the ultrasonic waves are transmitted through the rim and then reflected back through the rim by a suitable reflective surface 71.

As noted, the variations on the types of transmitters and receivers used in accordance with this invention may to some extent be based on the type of containers. It is appreciated that the lid may be foil, where the base is laminated or non-laminated. As an alternative, the lid may be laminated or non-laminated multilayer plastic and the base may be foil. Alternatively both the lid and the container may be multilayer plastic of either laminated or non-laminated construction.

Figure 5D:
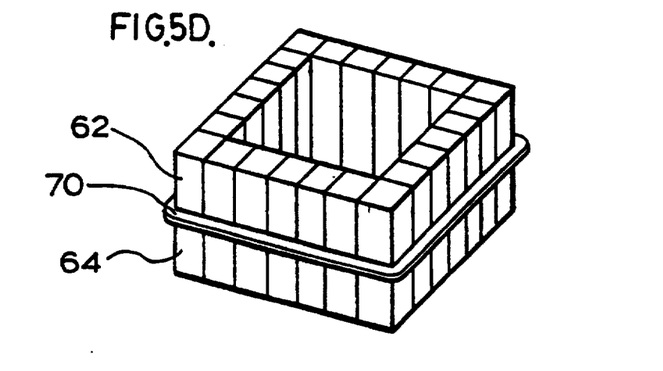

As shown in FIG. 5D, the continuous transducer array provides for a plurality of adjacent transmitters 62 with corresponding opposing receivers 64. The transmitters and receivers are positioned directly beside each other where their array is such to conform, in this embodiment, to the rectangular shape of the container rim 70. Although this array is cost intensive, it does provide for the best coverage in detecting the flaws in the container rim seal. Such detection may be warranted in situations where the contents are of significant value, such that the shelf life is an important consideration. It is appreciated that the reflective system functions in the same manner as the other transmitter and receiver systems. The transducer system is adapted to receive only wave energy reflected by the reflective surface 71. This system therefore requires the transmission of the wave energy through the rim to accomplish detection of minute particles in the seal which can cause flaws.

Figure 7:
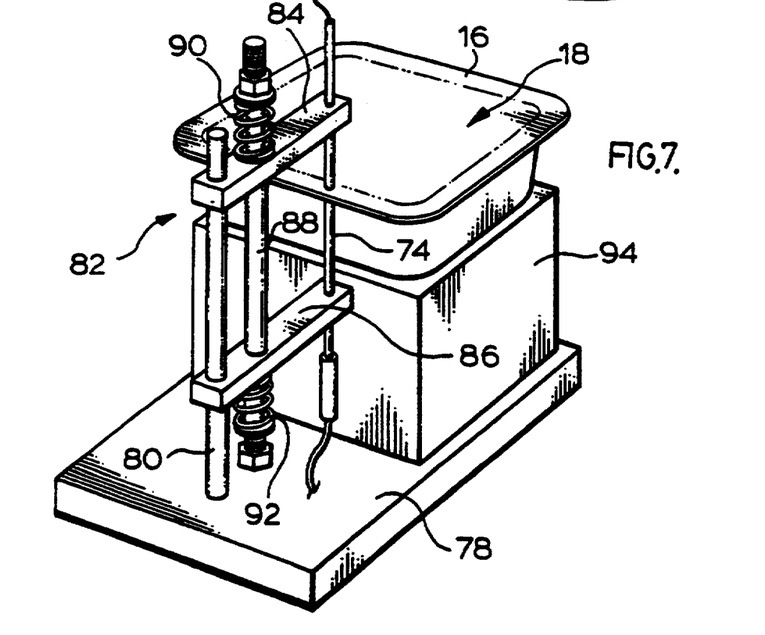
FIG. 7 is perspective view of an apparatus for positioning the single transmitter and receiver of FIG. 6 and a platform on which the container rests and is rotated to sense the entire perimeter of the container.

An example of an apparatus for positioning the transmitter 72 and the receiver 74 on the rim 16 of the container 18 is shown in FIG. 7. A base 78 supports a standard 80. A spring-loaded clip mechanism is provided as mounted on the standard 80. A clip mechanism 82 comprises a first support arm 84 to which the transmitter 72 is secured. A second support arm 86 is provided to which the receiver 74 is connected. A second bar 88 is provided having springs 90 and 92 at each end thereof and which extend through the arms 84 and 86. The springs 90 and 92 provide sufficient pressure on the arms 84 and 86 relative to their mounting on the standard 80 to locate the transmitter 72 and receiver 74 on opposing sides of the container rim. The transmitter and receiver are ultrasonically coupled to the container rim in accordance with the procedures of either FIGS. 3 or 4.

The container 18, as mounted on table 94, is rotated to pass the rectangular-shaped rim 16 between the transmitter and the receiver 72, 74. The table 94 is provided with a suitable cam mechanism to rotate the container through a prescribed pattern so that the entire circumference of the rim 16 is scanned. As with the scanning procedure of FIG. 6, the container is either continuously moved or sequentially moved to provide transmission of ultrasonic waves through the container rim and hence detect any flaws therein.

Figure 8:
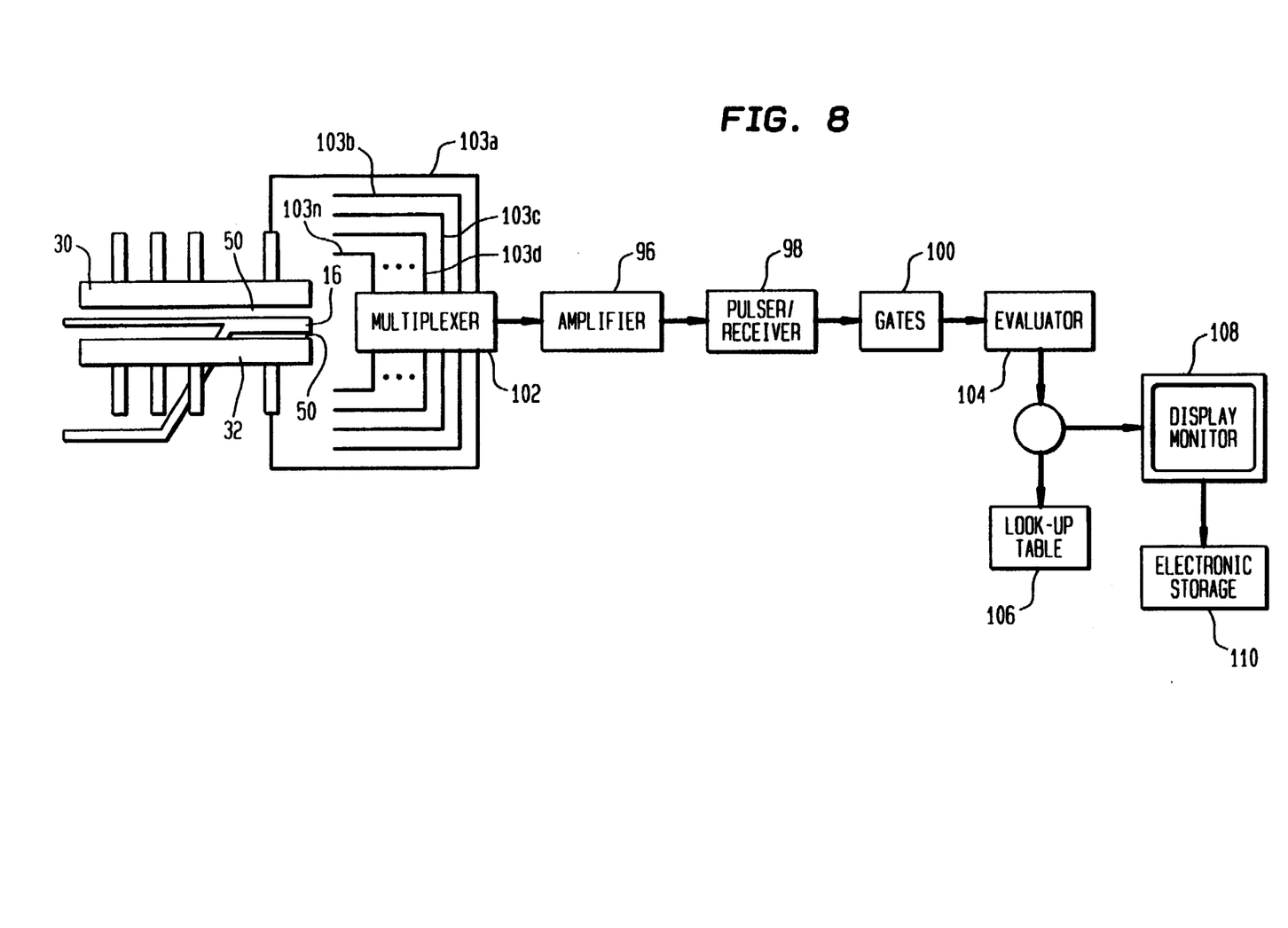
FIG. 8 is a block diagram representing the electronic components for generating and analyzing signals from the ultrasonic transducers.

A block diagram of the electronic components of the seal inspection apparatus is shown in FIG. 8. Inspection of the seal area of a flexible package is carried out by transmitting ultrasonic waves through the container rim. These waves are generated and detected by two arrays of ultrasonic transducers 30 and 32; i.e., transmitters and receivers, placed on the opposite sides of the container seal region 16. In order to improve the transfer of acoustic energy from the transducers, a thin layer of water 50, such as in FIG. 2, is maintained between the transducer surface and the seal surfaces. The generation and detection of the ultrasonic energy is achieved by a pulser/receiver 98 via an amplifier 96, such as is conventional with ultrasonic inspection devices. The pulser/receiver may produce 100/200 volts D.C. pulses at a pulse repetition frequency in the range of 1–10 kilohertz with a band width from 100 KHZ to 50 MHZ in a typical arrangement. The ultrasonic transducer array is connected to the signal generation and detection equipment via a multiplexer 102 which activates each transducer unit in the array sequentially as shown by multiple leads 103a, b, c, . . . n.

The signals detected by the transducers are rectified to produce a video signal. These signals are then passed through a series of gates 100, such that the signals which contain information about the seal region are windowed. The peak and the width of the windowed signal may then be evaluated at 104 and subsequently be subtracted from a reference signal taken from a look-up table 106. The look-up table is compiled from averaged signals from a container with known seal integrity. The difference of the signals may be indicated on a display monitor by color coded lights 102. The magnitude of such difference indicates the quality of the seal integrity. The difference, once exceeding a predetermined magnitude, indicates a flaw in the seal. This information may also be digitized by an "analog to digital" convertor for electronic storage and further analysis in unit 110.

The voltage signals generated by the gates 100 of the electronic system of FIG. 8 are shown in FIGS. 9(A,B), 9(C,D) and 9 (E,F). For each signal, the information which is considered relevant to determining defects is located in the center part of each graph. The right-hand side of the graph shows secondary effects, that is, stray echoes and are not considered relevant to the determination of a defect. When the container rim is free of defects, the first peak in the central portion of the graph is of considerable height. In each graph, a horizontal upper line defines signal magnitude which corresponds to a defect-free seal. Hence, when the height of the first peak is close to this upper line, then there is no defect. However, when the first peak appears considerably below the upper horizontal line, a defect is present.

Figure 9A:
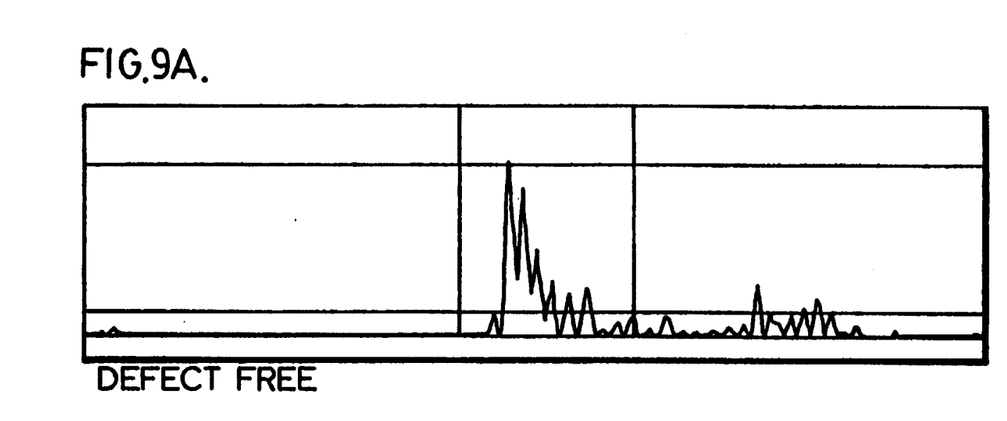
Figure 9B:
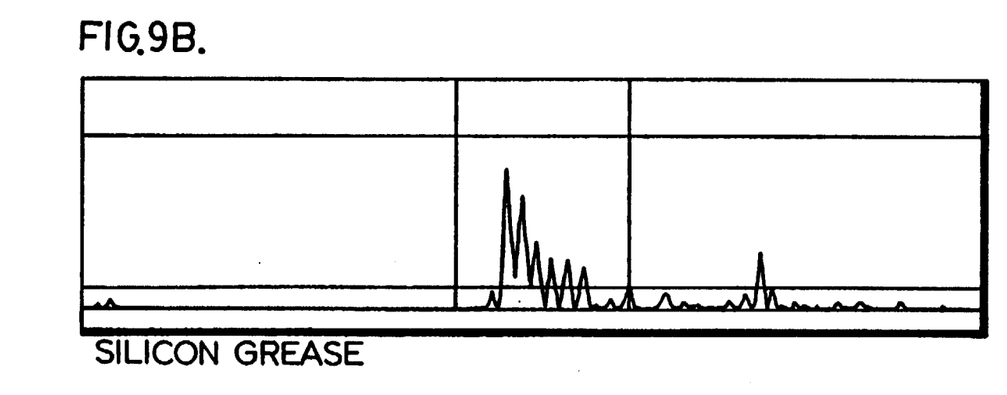
Figure 9C:
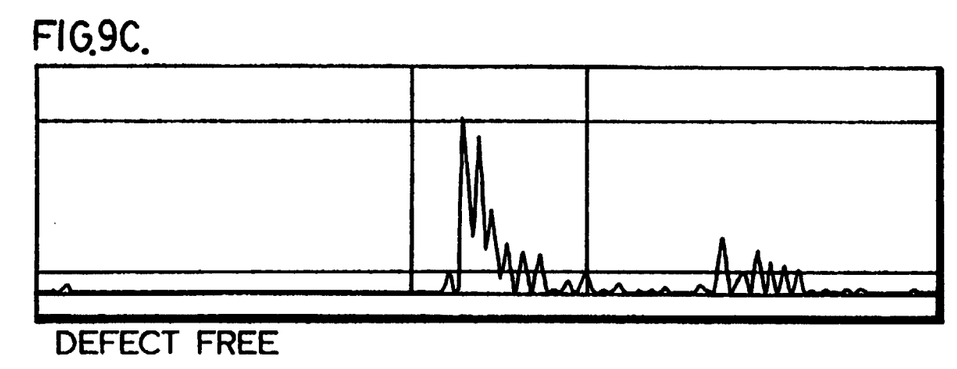
Figure 9D:
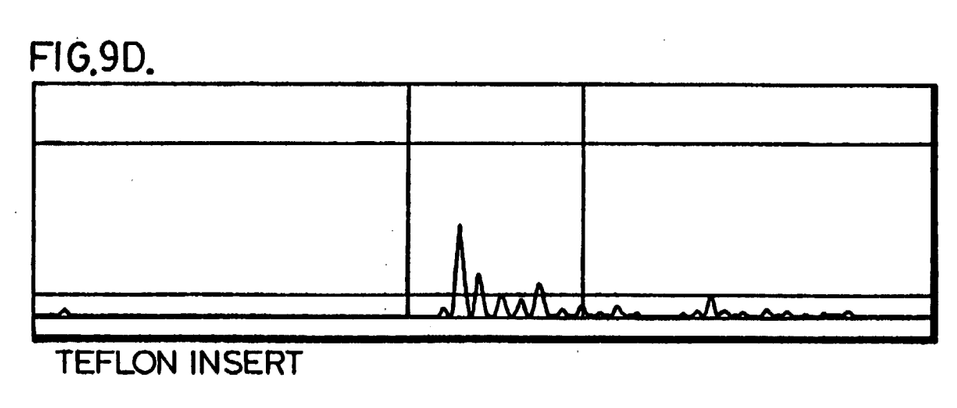

With reference to FIG. 9A, the signal generated by a defect-free rim demonstrates that the first significant peak is slightly above the upper horizontal line. However in FIG. 9B, the first significant peak is substantially below the upper horizontal line to indicate the presence of silicon grease in the seal area which has resulted in a defective seal. Similarly, in FIGS. 9C and 9D, the comparison of the defect and hence significantly lower first peak in FIG. 9D, graphically demonstrates the ability to detect Teflon in the seal. As shown in FIG. 9C with the defect-free rim, the first peak is well above that of the defective seal and as noted, is slightly above the upper horizontal line.

Figure 9E:
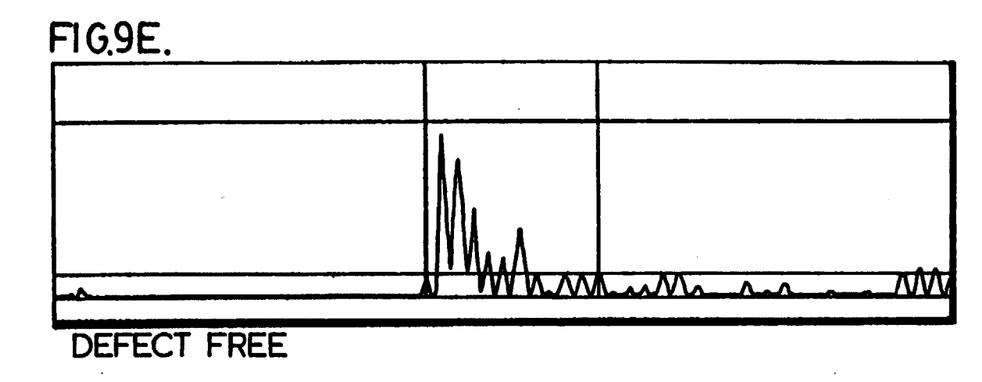
Figure 9F:
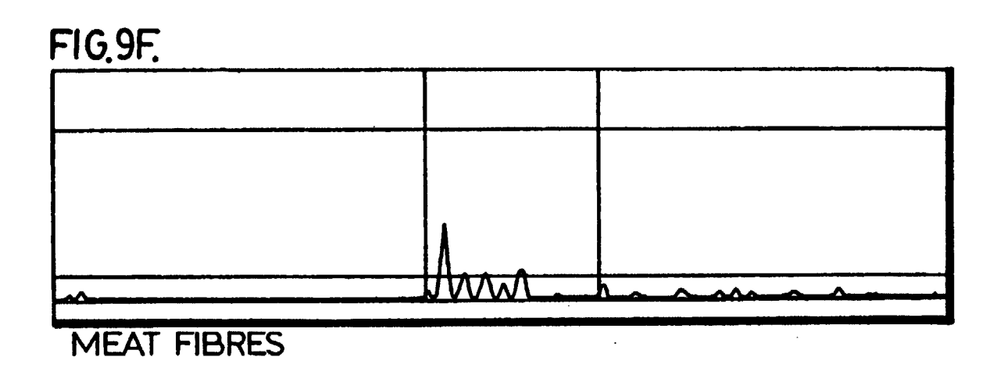

FIGS. 9E and 9F demonstrate the detection of meat fibers in the seal. Normally, this is very difficult to detect; however, with the system according to this invention, the presence of a meat fibre in the seal stands out significantly. In FIG. 9E, the defect-free rim has the first significant peak very close to the upper horizontal line. However in FIG. 9F, the first significant peak is roughly one-half the height of that in the defect-free rim to indicate the presence of meat fibre defects. Hence this invention is capable of detecting not only the very difficult to determine silicon and Teflon types of defects, but also the presence of very fine meat fibers in the seal.

It is understood, of course, that this invention is particularly suited to the measurement for meat fibres. This is the most common form of food which develops flaws in the seal. The above examples, however, also demonstrate the effectiveness of this invention in detecting silicon grease and Teflon. To demonstrate the sensitivity of the method with this type of sensitivity, it is appreciated that many other types of food contaminants which affect the quality of the seal can be measured with this invention. With the examples of FIGS. 9E and 9F, the tests were run with approximately one square mm of meat fibre mix positioned on the bond line and the bond line was then sealed using a transparent plastic lid material. This resulting defect in the seal is of such a minuscule nature to be barely visible to the naked eye. However, as demonstrated with respect to FIG. 9F, the flaw was easily detected by the process and apparatus of this invention.

As noted, the upper horizontal line in each of FIGS. 9A through 9F is used as a reference line to judge the height of the transmitted sound pulses. It is understood that, under actual production conditions, various techniques may be employed to determine the height of the horizontal line. For example, statistical process control may be employed using a representative sampling of the containers passed through the device. The desired confidence level can be calculated to position electronically the horizontal line. The distance between the two vertical lines of the peak would be set before hand on the instrument to define the time interval of interest. This distance would constitute a "gate" where the instrument used would be a normal form of a gated peak detector. Hence the position of the peak within the gate is irrelevant. A reject signal would be transmitted if any peak does not reach or go beyond the upper horizontal line.

Although preferred embodiments of the invention have been described herein in detail, it will be understood by those skilled in the art that variations may be made thereto without departing from the spirit of the invention or the scope of the appended claims.

We claim:

1. A method for determining bond integrity of a sealed package having a lid bonded to a container rim by detecting flaws in the bond between the lid and the container, said method comprising:
   i) positioning said container rim between an ultrasonic transmitter system and an ultrasonic receiver system; said transmitter system and said receiver system comprising an array of a plurality of transmitters and a corresponding plurality of receivers, said array having a spatial arrangement to correspond to a circumferential shape of said container rim and thereby locate said transmitters and receivers at locations about said container rim; each of said transmitters being offset laterally from a corresponding receiver;
   ii) ultrasonically coupling said transmitter system and said receiver system to said container;
   iii) transmitting ultrasound waves from said transmitter system through said container rim to said receiver system while said container rim remains stationary relative said transmitter system and said receiver system;
   iv) generating a voltage signal representative of said ultrasound waves received by said receiver system; and
   v) analyzing said voltage signal for predetermined signal characteristics representative of a flaw in said bond to identify a flawed package seal.

2. An apparatus for use in determining bond integrity of a sealed package having a lid bonded to a container rim, said apparatus comprising:
   i) spaced-apart opposing ultrasonic transmitter system and an ultrasonic receiver system, said transmitter system comprising an array of a plurality of transmitters and said receiver system comprising an array of a plurality of receivers, said array having a spatial arrangement to correspond to a circumferential shape of said container rim and thereby locate said transmitters and said receivers at locations about a container rim, each of said transmitters is offset laterally from a corresponding receiver;
   ii) means for positioning a container rim stationary between said ultrasonic transmitter system and said ultrasonic receiver system; and
   iii) means for ultrasonically coupling said transmitter system and said receiver system to a container rim.

3. A method for determining bond integrity of a sealed package having a lid bonded to a container rim by detecting flaws in the bond between the lid and the container, said method comprising:
   i) positioning said container rim between an ultrasonic transmitter system and an ultrasonic receiver system;
   ii) ultrasonically coupling said transmitter system and said receiver system to said container rim;
   iii) transmitting ultrasound waves from said transmitter system through said container rim to said receiver system;
   iv) generating a voltage signal representative of said ultrasound waves received by said receiver system;
   v) analyzing said voltage signal for predetermined signal characteristics representative of a flaw in said bond to identify a flawed package seal;
   vi) said transmitter system and said receiver system having an array of a plurality of transmitters and an array of a plurality of receivers, said array having a spatial arrangement to correspond to a circumferential shape of said container rim and thereby locate said transmitters and receivers at locations about said container rim, said array comprising two receivers for each transmitter, the two receivers being offset laterally relative to said transmitter.

4. An apparatus for use in determining bond integrity of a sealed package having a lid bonded to a container rim, said apparatus comprising:
   i) spaced-apart opposing ultrasonic transmitter system and an ultrasonic receiver system;
   ii) means for positioning a container rim between said ultrasonic transmitter system and said ultrasonic receiver system; and
   iii) means for ultrasonically coupling said transmitter system and said receiver system to a container rim; said transmitter system including an array of a plurality of transmitters and said receiver system comprising an array of a plurality of receivers, said array having a spatial arrangement to correspond to a circumferential shape of said container rim and thereby locate said transmitters and said receivers at locations about a container rim; wherein said array comprises two receivers for each transmitter, the two receivers being offset laterally relative to said transmitter.

* * * * *